United States Patent [19]

Kato et al.

[11] Patent Number: 4,948,491

[45] Date of Patent: Aug. 14, 1990

[54] OXYGEN SENSOR

[75] Inventors: Nobuhide Kato; Masanori Katsu, both of Aichi, Japan

[73] Assignee: NGK Insulators, Ltd., Japan

[21] Appl. No.: 382,580

[22] Filed: Jul. 20, 1989

[30] Foreign Application Priority Data

Jul. 30, 1988 [JP] Japan .......................... 63-100595[U]

[51] Int. Cl.$^5$ .......................................... G01N 27/409
[52] U.S. Cl. .................................. 204/424; 204/427; 204/428; 338/34
[58] Field of Search ............... 204/424, 425, 426, 427, 204/428, 429, 1 S; 338/34

[56]     References Cited
U.S. PATENT DOCUMENTS

| | | | |
|---|---|---|---|
| 4,141,813 | 2/1979 | Kita et al. | 204/428 |
| 4,588,494 | 5/1986 | Kato et al. | 204/426 |
| 4,591,423 | 5/1986 | Kato et al. | 204/428 |
| 4,642,174 | 2/1987 | Shibata | 204/408 |

FOREIGN PATENT DOCUMENTS 60-137336  9/1985  Japan .
60-150448 10/1985  Japan .

Primary Examiner—G. L. Kaplan
Attorney, Agent, or Firm—Arnold, White & Durkee

[57]     ABSTRACT

An oxygen sensor having construction of an upper open end portion plugged with a grommet through which lead wires are taken out of a protecting metallic cover. A resin grommet of a heat resistant resin such as Teflon, polyimide or the like is fitted in the upper open end portion of the metallic cover with a portion of the grommet being extended from upper open end portion of the metallic cover. A heat resistant non-metallic tube such as Teflon, polyimide, silicone rubber, fluororubber tube is closely fitted on the periphery of the extended portion of the resin grommet and the periphery of the upper end portion of the metallic cover and a metallic tube being closely fitted on the periphery of a portion of the non-metallic tube which is fitted on at least the metallic cover.

7 Claims, 2 Drawing Sheets

FIG._4
PRIOR ART
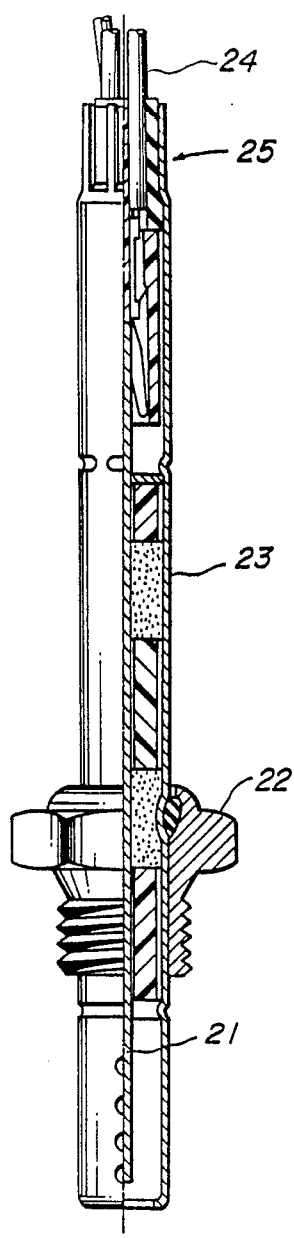
FIG._5
PRIOR ART
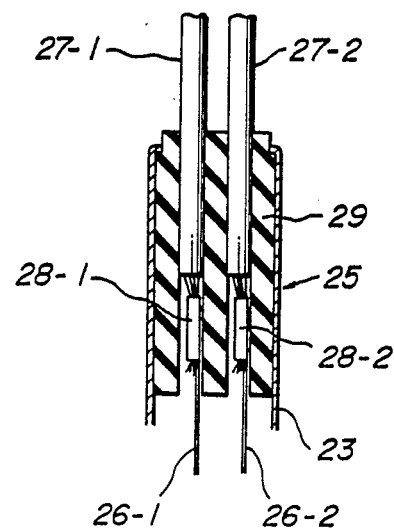

OXYGEN SENSOR

BACKGROUND OF THE INVENTION

1. Field of the Invention

The present invention relates to an oxygen sensor for detecting oxygen concentration in an exhaust gas discharged from internal combustion engines, and more particularly to an improved construction of an end portion of such an oxygen sensor.

2 Related Art Statement

Hitherto, there has been known an oxygen sensor as shown in FIG. 4, which comprises a sensor element 21 protected by a metallic cover 23, a metallic housing 22 for mounting the sensor on an outer wall of an internal combustion engine to expose an outer electrode of the sensor element to the exhaust gas to be measured, and at least one lead wire 24 extended through a rubber grommet fitted in an upper open end of the metallic cover 23 at an upper end portion 25 of the sensor for transmitting an oxygen concentration detecting signal from the sensor element 21.

The structure of the conventional upper end portion 25 of the sensor is shown on an enlarged scale in FIG. 5. Referring to FIG. 5, lead terminals 26-1 and 26-2 are longitudinally extended in the upper end portion 25 to electrically connect to the electrode terminals of the sensor element (not shown). Lead wires 27-1 and 27-2 are extended through the rubber grommet 29 to be inserted inside the sensor and connected to the upper end of the lead terminals 26-1 and 26-2, respectively, at connecting portions 28-1 and 28-2 by means of caulking. In a case where the oxygen sensor includes a heater, a lead wire connected to the heater is also extended through the rubber grommet 29 at the upper end portion of the oxygen sensor. The rubber grommet 29 is made of silicon rubber or fluororubber.

Such a rubber grommet 29 is sometimes heated to an abnormally high temperature by radiant heat from exhaust manifolds and exhaust pipes, which are heated to a high temperature when the engine of a vehicle is suddenly stopped after running at a high speed. When the vehicle is running, however, there is no abnormal heating problem since the rubber grommet 29 is cooled by the air.

When the rubber grommet 29 is heated to a temperature higher than 200° C. in particular higher than 230° C., a harmful gas is generated from the rubber grommet 29 and adversely affects the inner electrode of the sensor element in that the partial pressure of the oxygen in the reference air at the inner electrode is varied by the harmful gas to provide an abnormal output. Consequently, the rich voltage and lean voltage are reduced or the inner electrode of the oxygen sensor element is corroded by the harmful gas, thereby reducing the electromotive force generated by the sensor (the rich voltage and lean voltage are reduced).

In the former, the output signal of the sensor is recovered to a normal condition by introducing fresh air into the inside of the metallic cover 23, but in the latter, the output signal of the sensor can not be recovered to a normal condition even if a fresh air is introduced into the metallic cover, since the electrode has been damaged.

In order to solve the aforementioned problems, it has been proposed to use a resin grommet made of Teflon (Polytetrafluoroethylene, Registered Trade Mark) or polyimide instead of a rubber grommet since such a resin does not generate harmful gases even at a temperature of 300° C. However, a problem occurs that when a grommet made of Teflon or polyimide is heat cycled, a gap is formed between the outer peripheral surface of the grommet of Teflon or polyimide and the inner surface of the metallic cover as shown in FIG. 5. The gap is a result of a difference in coefficient of thermal expansion between the metallic cover and the resin grommet of Teflon or polyimide. The gap allows water to leak into the inside of the sensor thus appealing the partial pressure of oxygen of the reference air upon evaporation of water. As a result, the electromotive force.

SUMMARY OF THE INVENTION

It is an object of the present invention to provide an oxygen sensor including an improved construction of an end portion adapted for preventing a continuous gap from occurring between the resin grommet and the end portion of the metallic cover without generating of harmful gas from the resin grommet, thereby preventing reduction of the electromotive force even if the upper end of the sensor is exposed to an abnormally high temperature.

The present invention includes an oxygen sensor comprising an oxygen sensor element for detecting oxygen concentration in an exhaust gas, a lead wire for transmitting an oxygen concentration detecting signal from the oxygen sensor element and a metallic cover for protecting the oxygen sensor element. A portion of the lead wire is extended inside the metallic cover, a resin grommet of a heat resistant resin such as Teflon, polyimide and the like is fitted in an upper open end portion of the metallic cover. The lead wire is projects out of the metallic cover through the upper open end and a portion of the resin grommet extends from the upper end of the metallic cover. A heat resistant non-metallic tube is closely fitted on the periphery of the extended portion of the resin grommet and the periphery of the upper end portion of the metallic cover, and a metallic tube is closely fitted on the periphery of a portion of the non-metallic tube which is fitted on at least the metallic cover.

The resin grommet is fitted in the upper end portion of the metallic cover and then the upper end portion is reduced to closely fit on the periphery of the resin grommet, thereby providing good mechanical strength at the end portion of the sensor. The periphery of the end portion of the metallic cover and the periphery of the resin grommet extended from the end of the metallic cover are covered with the heat resistant non-metallic tube and are further covered with the metallic tube. Accordingly, the formation of a continuous gap between the grommet and the end portion of the metallic cover ia prevented and consequently, leakage of water into the inside of the oxygen sensor through such a gap is also prevented.

When the grommet is of Teflon, the heat resistant resin tube of Teflon is preferably used because of the same coefficient of thermal expansion.

The invention will be described in greater detail with reference to the accompanying drawings.

BRIEF DESCRIPTION OF THE DRAWINGS

FIG. 4 is a partial sectional view illustrating a construction of an oxygen sensor of the Prior Art; and FIG. 5 is a sectional view illustrating a construction of the upper end portion of the oxygen sensor shown in FIG. 4.

DETAILED DESCRIPTION OF THE PREFERRED EMBODIMENTS

Figure 1:
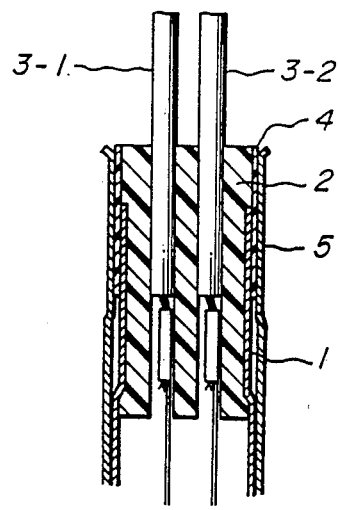
FIG. 1 is a sectional view of an embodiment of the upper end portion of an oxygen sensor according to the invention.

FIG. 1 illustrates an embodiment of the upper end portion of an oxygen sensor according to the invention.

Referring to FIG. 1, the upper end portion of a metallic cover 1 for protecting a sensor element is closely fitted on the periphery of a heat resistant resin grommet 2 of Teflon. A portion of the grommet is extended from the upper end of the metallic cover 1. Lead wires 3-1 and 3-2 are extended out of the inside of the sensor through the grommet 2. The grommet 2 is fitted in the upper end portion of the metallic cover 1, which is then reduced to be closely fitted on the periphery of the grommet. A resin tube 4 of shrinkable Teflon is fitted on the periphery of the extended portion of the resin grommet 2 and the periphery of the upper end portion of the metallic cover 1 and then heated to be closely fitted on the peripheries of the resin grommet 2 and the metallic cover 1. On the resin tube 4 of Teflon is fitted a metallic tube 5 which is then reduced to be closely fitted on the periphery of the resin tube 4. The metallic tube 5 is fixed at its lower end to the metallic cover 1 by means of caulking (not shown). In this embodiment, since a grommet of Teflon is used, no harmful gas is generated from the grommet and the waterproof nature of the end portion is not deteriorated by heating to an abnormally high temperature.

The reason why the waterproof nature is not deteriorated will now be described with reference to the construction of the end portion shown in FIG. 1.

The waterproof nature of the end portion is deteriorated owing to a gap occurring between the grommet and the metallic cover due to a difference in the thermal expansions of Teflon and the metal when subjected to a heat cycle (for example 300° C. ↔room temperature: 25° C.). Firstly, the gap occurring between the grommet 2 and the metallic cover 1 is considered. In a sensor which has been assembled, there is no gap between the grommet 2 of Teflon and the metallic cover 1 until the sensor is subjected to heat. When the sensor is heated to high temperatures (for example 300° C.), no gap occurs since the coefficient of thermal expansion of Teflon is larger than that of the metallic cover (SUS 304), but the grommet 2 is longitudinally elongated by plastic deformation within the metallic cover 1 since the Teflon grommet 2 has little elasticity. Subsequently, when the sensor is cooled to the room temperature, a gap occurs between the metallic cover 1 and the grommet 2 in the same manner as the prior art, since the coefficient of thermal expansion of Teflon is larger than that of SUS 304.

In a case where the outer diameter of the Teflon grommet is 10 mm$\phi$, the coefficient of thermal expansion of Teflon is $150 \times 10^{-6}$/°C. and the coefficient of thermal expansion of SUS 304 is $18 \times 10^{-6}$/°C. and the temperature is varied from 300° C. to 25° C., the amount of the gap is worked out as follows:

Amount of gap $=(150-18) \times 10^{-6} \times (300-25) \times 10 = 0.36$ (mm).

While gaps occur between the Teflon tube 4 and the metallic cover 1 and also the metallic tube 5, respectively in the same mechanism, since the tube 4 is sandwiched between metallic members 4 and 5 having the same coefficient of thermal expansion and is as thin as 0.3 mm, the gap is very small. Accordingly, on the similar basis the amount of each of gap is worked out as follows:

Amount of each of gap $=(150-18) \times 10^{-6} \times (300-25) \times 0.3 = 0.01$ (mm).

Since the gap is so small, water can not leak into the inside of the sensor.

Furthermore, considering the possibility of a gap at the extended portion of the Teflon grommet 2, there is no gap between the Teflon grommet 2 and the Teflon tube 4 because of the same coefficient of thermal expansion. Although a gap of about 0.4 mm occurs between the Teflon tube 4 and the metallic tube 5, water can not leak into the inside of the sensor since the gap does not communicate with the inside of the sensor It is understood from the above, that the concept of the invention lies in the use of a thin Teflon member interposed between metallic members having substantially the same coefficient of thermal expansion to limit an amount of gap occurring at the end portion, to thereby shut down a passageway of water communicating to the inside of the sensor. The thickness of the Teflon tube is preferably not greater than 1 mm.

Figure 2:
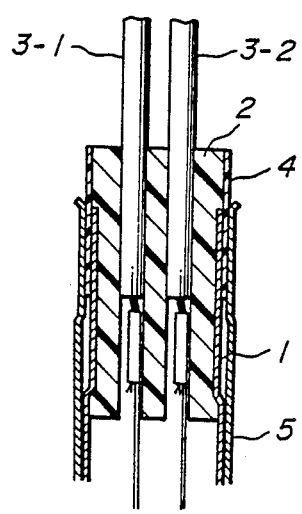
FIG. 2 is a sectional view of other embodiment similar to FIG. 1.

The present invention, without being restricted to the aforementioned embodiment shown in FIG. 1, can be carried out in various forms. For example, the resin tube 4 may be a normal Teflon tube instead of shrinkable Teflon tube. In this case, the metallic tube must be caulked in the extended portion of the Teflon grommet to fit the Teflon tube 4 on the grommet. In case of using the shrinkable Teflon tube, it need not be caulked to the metallic tube 5 in the extended portion of the grommet 2 as shown in FIG. 2, but the Teflon tube is preferably protected by the metallic tube 5.

The materials of the metallic cover 1 and the metallic tube 5 are preferably the same material or of the same coefficient of thermal expansion, but the materials do not necessarily have to be the same or have the same coefficient of thermal expansion. Thus, a combination of different materials can be used for the metallic cover 1 and the metallic tube 5 if a difference between the coefficient of thermal expansion of the metallic material to be combined is sufficiently smaller than a difference of coefficient of thermal expansion between each metallic material and Teflon, for example a combination of SUS 304 and SUS 430 (difference of $18 \times 10^{-6}$/°C. and $11 \times 10^{-6}$/° C.).

The materials of the tube 4 may be rubber based materials such as silicone rubber, fluororubber, but is preferable Teflon or polyimide, since such resins have the property that a decrease in weight at high temperatures (for example 250° C.~300° C.) is small. The material of the tube will be selected in accordance with the conditions of use, such as a temperature of the portion of the tube. Although the rubber material such as silicone rubber or fluororubber generates a harmful gas, the harmful gas hardly leaks into the inside of the sensor since the tube 4 is arranged in the outside of the metallic cover. Therefore, various rubbers can be used for the tube 4 in so far as, the heat resistance of rubber is permissible. When a shrinkable rubber tube is used, the tube 4 is not required to be fixed by the metallic tube 5 since the rubber tube 4 can elastically closely fit on the peripheries of the metallic cover and the extended portion of the Teflon grommet.

Figure 3:
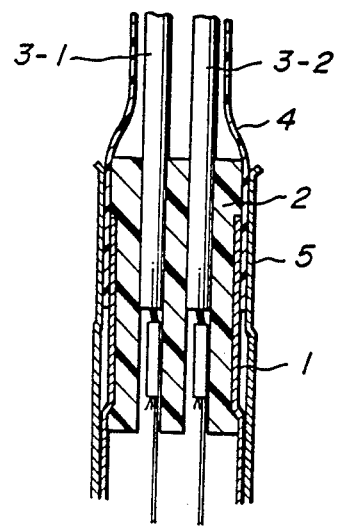
FIG. 3 is a sectional view of a third embodiment similar to FIG. 1.

As shown in a third embodiment of the invention (FIG. 3), the Teflon tube 4 may be used for protecting the lead wires 3-1, 3-2.

The material for the Teflon grommet, polyimide grommet, Teflon tube, polyimide tube, silicone rubber tube and fluororubber tube may be mixed with glass fibers to improve those heat resistance. The metallic tube may be fixed to the metallic cover at a position just under the lower end of the Teflon tube. The oxygen sensor may be an all range oxygen sensor or the other using an oxygen ionic conductive solid electrolyte with an inner electrode having a reference oxygen concentration. The teflon tube may be integrally formed with the Teflon grommet.

What is claimed is:

1. An oxygen sensor comprising an oxygen sensor element for detecting oxygen concentration in an exhaust gas, at least one lead wire for transmitting off an oxygen concentration detecting signal from the oxygen sensor element and a metallic cover for protecting the oxygen sensor element, a portion of the lead wire being extended inside the metallic cover, said sensor further comprising a resin grommet of a heat resistant resin being fitted in an upper open end portion of the metallic cover through which end the lead wire is taken out of the metallic cover with a portion of the resin grommet being extended from the upper end of the metallic cover, a heat resistant non-metallic tube being fitted on the periphery of the extended portion of the resin grommet and the periphery of the upper end portion of the metallic cover and a metallic tube being fitted on the periphery of a portion of the non-metallic tube which is fitted on at least the metallic cover.

2. An oxygen sensor claimed in claim 1, wherein the heat resistant resin grommet is of polytetrafluoroethylene or polyimide.

3. An oxygen sensor claimed in claim 1, wherein the heat resistant non-metallic tube is of shrinkable polytetrafluorethylene or polyimide.

4. An oxygen sensor claimed in claim 1 wherein the heat resistant non-metallic tube is silicone rubber or fluororubber.

5. An oxygen sensor claimed in claim 1, wherein the metallic tube has substantially the same coefficient of thermal expansion as that of the metallic cover.

6. An oxygen sensor claimed in claim 1, wherein the metallic tube is fitted on all the periphery of the non-metallic tube.

7. An oxygen sensor claimed in claim 1, wherein the non-metallic tube is extended over the outer end of the resin grommet to protect the lead wire extended out of the grommet.

* * * * *